United States Patent
Matsuo et al.

(10) Patent No.: US 9,662,433 B2
(45) Date of Patent: May 30, 2017

(54) PRESSURE DETECTION DEVICE OF LIQUID FLOW ROUTE

(71) Applicant: Nikkiso Company Limited, Tokyo (JP)

(72) Inventors: Sumiaki Matsuo, Shizuoka (JP); Kazumi Yokoyama, Shizuoka (JP); Kunihiko Akita, Shizuoka (JP)

(73) Assignee: NIKKISO COMPANY LIMITED, Tokyo (JP)

( * ) Notice: Subject to any disclaimer, the term of this patent is extended or adjusted under 35 U.S.C. 154(b) by 476 days.

(21) Appl. No.: 14/186,193

(22) Filed: Feb. 21, 2014

(65) Prior Publication Data

US 2014/0219829 A1   Aug. 7, 2014

Related U.S. Application Data

(63) Continuation of application No. PCT/JP2012/070614, filed on Aug. 13, 2012.

(30) Foreign Application Priority Data

Aug. 22, 2011   (JP) ................................. 2011-180170

(51) Int. Cl.
*A61M 1/36* (2006.01)
*F04B 43/12* (2006.01)
(Continued)

(52) U.S. Cl.
CPC .......... *A61M 1/367* (2013.01); *A61M 1/1039* (2014.02); *A61M 1/3639* (2013.01);
(Continued)

(58) Field of Classification Search
CPC ... G01L 9/0002; A61M 1/167; A61M 1/1037; A61M 1/1039; A61M 1/3639;
(Continued)

(56) References Cited

U.S. PATENT DOCUMENTS 3,046,788 A * 7/1962 Laimins ................ G01L 9/0002
338/4
4,090,404 A * 5/1978 Dupont ................ F02M 65/003
73/114.43
(Continued)

FOREIGN PATENT DOCUMENTS

JP     S64-022357     2/1989
JP     WO94/28309     8/1994
(Continued)

OTHER PUBLICATIONS

Extended European Search Report dated Apr. 8, 2015 for Application No. 12826289.

(Continued)

*Primary Examiner* — Theodore Stigell
*Assistant Examiner* — Jon Hoffmann
(74) *Attorney, Agent, or Firm* — The Dobrusin Law Firm, P.C.

(57) ABSTRACT

A pressure detection device of a liquid flow route is provided which detects a pressure of an arterial blood circuit consisting of a flexible tube, a portion of which is connected to a peristaltically-actuated tube that can cause an internal liquid to flow by being compressed in a radial direction and being peristaltically actuated in a longitudinal direction in a roller of a blood pump, and which enables a predetermined liquid to be circulated. The pressure detection device includes a load sensor that detects radial displacement of the peristaltically-actuated tube.

15 Claims, 8 Drawing Sheets

(51) Int. Cl.
*G01L 9/00* (2006.01)
*A61M 1/10* (2006.01)

(52) U.S. Cl.
CPC ...... *F04B 43/1261* (2013.01); *F04B 43/1284* (2013.01); *G01L 9/0002* (2013.01); *A61M 2205/3331* (2013.01)

(58) Field of Classification Search
CPC .. A61M 2205/3331; A61M 2205/3351; A61M 2205/3355; A61M 5/14232; A61M 5/16854; A61M 1/10; A61M 1/1043; F04B 43/1284; F04B 43/1261; F04B 43/12; F04B 43/1253; F04B 43/08; F04B 43/0072; F04B 43/15; F04B 43/1238; F04B 43/1292; F04B 49/00; F04B 53/22; F04B 49/08; F04B 2205/05; F04B 2207/01
USPC ....... 417/477.3, 477.7, 477.8, 477.9, 477.11, 417/477.12, 474, 476; 604/6.11
See application file for complete search history.

(56) References Cited

U.S. PATENT DOCUMENTS

| | | | | |
|---|---|---|---|---|
| 4,460,355 A * | 7/1984 | Layman | ............ | A61M 5/16859 222/40 |
| 4,534,756 A * | 8/1985 | Nelson | ............ | A61M 5/16859 604/505 |
| 4,743,228 A * | 5/1988 | Butterfield | ........ | A61M 5/16859 604/245 |
| 4,762,518 A * | 8/1988 | Kreinick | ............ | A61M 5/16854 250/577 |
| 4,784,576 A * | 11/1988 | Bloom | .................. | A61M 5/142 128/DIG. 13 |
| 5,024,099 A * | 6/1991 | Lee | ....................... | G01L 9/0002 361/283.2 |
| 5,215,450 A * | 6/1993 | Tamari | ................ | A61M 1/0031 138/119 |
| 5,336,051 A * | 8/1994 | Tamari | ................ | A61M 1/0031 417/19 |
| 5,356,378 A * | 10/1994 | Doan | ................ | A61M 5/16859 128/DIG. 13 |
| 5,380,172 A * | 1/1995 | Ulbing | ................ | F04B 43/1223 417/360 |
| 5,429,483 A * | 7/1995 | Tamari | ................ | A61M 1/0031 417/307 |
| 5,720,721 A | 2/1998 | Dumas et al. | | |
| 5,813,842 A * | 9/1998 | Tamari | ................ | A61M 1/0031 417/477.1 |
| 5,814,004 A * | 9/1998 | Tamari | ................ | A61M 1/0031 251/10 |
| 5,927,951 A * | 7/1999 | Tamari | ................ | A61M 1/0031 417/476 |
| 6,039,078 A * | 3/2000 | Tamari | ................ | A61M 1/0031 138/30 |
| 7,935,912 B2 * | 5/2011 | Arima | .................... | F23Q 7/001 219/260 |
| 9,004,886 B2 * | 4/2015 | Beck | .................. | F04B 43/0081 417/423.14 |
| 2002/0151838 A1 | 10/2002 | Beck et al. | | |
| 2003/0214412 A1 * | 11/2003 | Ho | .................... | A61M 5/14228 340/611 |
| 2008/0154095 A1 * | 6/2008 | Stubkjaer | ........... | A61M 3/0258 600/156 |
| 2010/0049134 A1 * | 2/2010 | Schuman, Jr. | ...... | A61M 1/0066 604/153 |
| 2010/0106466 A1 * | 4/2010 | Frohlich | ............ | G06F 17/5086 703/2 |
| 2010/0203179 A1 * | 8/2010 | Kaushik | ................ | A61K 36/53 424/774 |
| 2011/0130741 A1 * | 6/2011 | Miles | .................. | G01N 29/032 604/500 |
| 2011/0230814 A1 | 9/2011 | Kopperschmidt et al. | | |
| 2012/0082576 A1 * | 4/2012 | Beck | .................. | F04B 43/0081 417/474 |

FOREIGN PATENT DOCUMENTS

| | | | |
|---|---|---|---|
| JP | H08-510812 A | 11/1996 | |
| JP | 2003-265601 | 9/2003 | |
| JP | 2004-049494 | 2/2004 | |
| JP | 2004-187990 | 7/2004 | |
| WO | 94/28309 A1 | 12/1994 | |
| WO | WO 9428309 A1 * | 12/1994 | .......... A61M 1/3621 |
| WO | 2010/020380 A1 | 2/2010 | |

OTHER PUBLICATIONS

Translation of International Search Report, Application No. PCT/JP2012/070614, dated Sep. 11, 2012.

* cited by examiner

PRESSURE DETECTION DEVICE OF LIQUID FLOW ROUTE

FIELD

The present invention relates to a pressure detection device of a liquid flow route, which detects clogging of the liquid flow route consisting of a flexible tube, a portion of which is connected to a peristaltically-actuated tube that can cause an internal liquid to flow by being compressed in a radial direction and by being peristaltically actuated in a longitudinal direction in a peristaltic unit of a peristaltic pump, and which enables a predetermined liquid to be circulated.

BACKGROUND

A general blood circuit used in hemodialysis treatment is mainly configured to include an arterial blood circuit in which an arterial puncture needle is attached to a distal end thereof and a venous blood circuit in which a venous puncture needle is attached to a distal end thereof. The blood circuit is configured so that a blood purifier such as a dialyzer can be connected to each base end of the arterial blood circuit and the venous blood circuit. A peristaltic blood pump is arranged in the arterial blood circuit and the blood pump is rotated in a state where both of the arterial puncture needle and the venous puncture needle puncture a patient. In this manner, blood is collected through the arterial puncture needle and the blood is caused to flow in the arterial blood circuit and is introduced to the dialyzer. The blood purified by the dialyzer is configured to flow in the venous blood circuit and to return to a body of the patient internally via the venous puncture needle so as to perform dialysis treatment.

In addition, a negative pressure detection device (pressure detection device) which usually detects a negative pressure is connected to an upstream side from the blood pump in the arterial blood circuit. The negative pressure detection device in the related art which consists of a member which is a so-called pillow configured to include a flexible hollow member having an internal space with a predetermined capacity. If the blood flowing in the arterial blood circuit has the negative pressure, the negative pressure detection device is configured so as to be bent in a direction where a front surface portion and a rear surface portion are close to each other (for example, refer to PTL 1). Then, for example, it is possible to detect the negative pressure by bringing a probe of the negative pressure detection device into contact with the front surface portion and the rear surface portion. One example may be found in PTL 1 Japanese Unexamined Patent Application Publication No. 2003-265601, incorporated by reference herein for all purposes.

SUMMARY

However, with regard to the pressure detection device in the related art, the flexible hollow member having the space with the predetermined capacity needs to be connected to the blood circuit (arterial blood circuit) in which the blood flows, thereby causing a problem in that the blood is likely to stagnate inside the flexible hollow member. In addition, a separate flexible hollow member needs to be connected to the blood circuit, thereby causing a problem in that the manufacturing cost of the blood circuit is increased and the capacity of a liquid flow route in the blood circuit (priming volume) is increased. Without being limited to the pressure detection device in the blood circuit, the problems can generally occur in pressure detection devices which can detect a pressure of a liquid flow route which enables a predetermined liquid to be circulated. Accordingly, solutions to the problems are required.

The present invention is made in view of the above-described circumstances, and aims to provide a pressure detection device which can suppress stagnation of a circulating liquid and decrease the manufacturing cost and the capacity of a liquid flow route.

According to the invention described herein, there is provided a pressure detection device of a liquid flow route, which detects a pressure of a liquid flow route which consists of a flexible tube, a portion of which is connected to a peristaltically-actuated tube that can cause an internal liquid to flow by being compressed in a radial direction and by being peristaltically actuated in a longitudinal direction in a peristaltic unit of a peristaltic pump, and which enables a predetermined liquid to be circulated. The pressure detection device includes a displacement detection device that detects radial displacement of the peristaltically-actuated tube.

According to the invention described in the teachings herein and, in the pressure detection device of a liquid flow route described in the teachings herein, the peristaltic pump includes a gripping device which grips the peristaltically-actuated tube attached to the peristaltic pump, and the displacement detection device can detect radial displacement of a portion gripped by the gripping device.

According to the invention described in the teachings herein and, in the pressure detection device of a liquid flow route described in the teachings herein, the gripping device has a gripping piece which can grip the peristaltically-actuated tube by radially pressing the peristaltically-actuated tube and a biasing device which biases the gripping piece against the peristaltically-actuated tube side. The displacement detection device detects a load applied to a fixing end side of the biasing device and detects the radial displacement of the peristaltically-actuated tube used on the detected load.

According to the invention described in the teachings herein, in the pressure detection device of a liquid flow route described in the teachings herein, the gripping device has a gripping piece which can grip the peristaltically-actuated tube by radially pressing the peristaltically-actuated tube and a biasing device which biases the gripping piece against the peristaltically-actuated tube side. The displacement detection device is arranged in a portion opposing the gripping piece by interposing the peristaltically-actuated tube therebetween, detects a pressure applied to a side surface of the peristaltically-actuated tube pressed by the gripping piece, and detects the radial displacement of the peristaltically-actuated tube based on the detected pressure.

According to the invention described in the teachings herein and, in the pressure detection device of a liquid flow route described in the teachings herein, the gripping device has an upstream side gripping device which grips an upstream side of the peristaltically-actuated tube and a downstream side gripping device which grips a downstream side of the peristaltically-actuated tube. The displacement detection device is arranged in either the upstream side gripping device or the downstream side gripping device according to a portion for detecting a pressure of the liquid flow route.

According to the invention described in the teachings herein and, in the pressure detection device of a liquid flow route described in the teachings herein, the peristaltically-actuated tube is connected to an intermediate portion in an arterial blood circuit for extracorporeally circulating blood of a patient during blood purification treatment. The peristaltic pump consists of a blood pump which can cause the blood to flow in the arterial blood circuit.

According to the invention described in the teachings herein and, the pressure detection device of a liquid flow route described in the teachings herein further includes a blood removal state detection device that can detect a blood removal state by estimating a pressure change in the liquid flow route from a distal end of the arterial blood circuit to the peristaltically-actuated tube, based on the radial displacement of the peristaltically-actuated tube which is detected by the displacement detection device when extracorporeally circulating the blood.

According to the invention described in the teachings herein and, in the pressure detection device of a liquid flow route described in the teachings herein, the blood removal state detection device has a blood removal defect ratio arithmetic device which obtains a radial displacement ratio of the peristaltically-actuated tube based on a detection value of the displacement detection device, and which obtains a blood removal defect ratio from the radial displacement ratio of the peristaltically-actuated tube by using a relationship between the pre-obtained radial displacement ratio of the peristaltically-actuated tube and the blood removal defect ratio.

According to the invention described in the teachings herein and, the pressure detection device of a liquid flow route described in the teachings herein further includes an actual blood flow rate arithmetic device that obtains a flow rate of the blood which is actually caused to flow by the rotation of the blood pump, based on the blood removal defect ratio obtained by the blood removal defect ratio arithmetic device and a setting blood flow rate obtained by a setting rotation speed of the blood pump.

According to the invention described in the teachings herein and, the pressure detection device of a liquid flow route described in the teachings herein further includes an informing device that can provide information under a condition that the blood removal defect ratio obtained by the blood removal defect ratio arithmetic device or the actual blood flow rate obtained by the actual blood flow rate arithmetic device is beyond a setting value which is set in advance.

According to the invention described in the teachings herein and in the pressure detection device of a liquid flow route described in the teachings herein, the peristaltically-actuated tube is connected to an intermediate portion of a substitution circulation route for circulating a substitution during blood purification treatment. The peristaltic pump consists of a substitution pump which can cause the substitution to flow in the substitution circulation route.

According to the invention described in the teachings herein, there is provided a peristaltic pump including the pressure detection device of a liquid flow route which is described in the teachings herein.

According to the invention described in the teachings herein, there is provided a blood purification apparatus including the peristaltic pump described in the teachings herein.

According to the invention described in the teachings herein, the pressure of the liquid flow route can be detected by the displacement detection device that detects the radial displacement of the peristaltically-actuated tube. Thus, a separate device for detecting the pressure no longer needs to be connected to the liquid flow route. Therefore, it is possible to suppress stagnation of the circulating liquid, and it is possible to reduce the manufacturing cost and the capacity of the liquid flow route.

According to the invention described in the teachings herein, the peristaltic pump includes the gripping device which grips the peristaltically-actuated tube attached to the peristaltic pump. The displacement detection device can detect the radial displacement of a portion gripped by the gripping device. Thus, the peristaltically-actuated tube is attached to the peristaltic pump and is gripped by the gripping device so that the peristaltically-actuated tube is attached to the pressure detection device. Therefore, health care workers can reduce the burden of work.

According to the invention described in the teachings herein, the gripping device has the gripping piece which can grip the peristaltically-actuated tube by radially pressing the peristaltically-actuated tube and the biasing device which biases the gripping piece against the peristaltically-actuated tube side. The displacement detection device detects the load applied to the fixing end side of the biasing device and detects the radial displacement of the peristaltically-actuated tube based on the detected load. Therefore, the biasing device in the peristaltic pump can be provided with both of a function for generating gripping force with respect to the peristaltically-actuated tube with increased force and a function for detecting the pressure of the liquid flow route.

According to the invention described in the teachings herein, the gripping device has the gripping piece which can grip the peristaltically-actuated tube by radially pressing the peristaltically-actuated tube and the biasing device which biases the gripping piece against the peristaltically-actuated tube side. The displacement detection device is arranged in a portion opposing the gripping piece by interposing the peristaltically-actuated tube therebetween, detects a pressure applied to a side surface of the peristaltically-actuated tube pressed by the gripping piece and detects radial displacement of the peristaltically-actuated tube based on the detected pressure. Therefore, the displacement detection device in the peristaltic pump can be provided with both of a function for receiving pressing force against the peristaltically-actuated tube and a function for detecting the pressure of the liquid flow route.

According to the invention described in the teachings herein, the gripping device has the upstream side gripping device which grips the upstream side of the peristaltically-actuated tube and the downstream side gripping device which grips the downstream side of the peristaltically-actuated tube. The displacement detection device is arranged in either the upstream side gripping device or the downstream side gripping device according to the portion for detecting the pressure of the liquid flow route. Therefore, it is possible to more accurately detect a pressure of a desired portion in the liquid flow route.

According to the invention described in the teachings herein, the peristaltically-actuated tube is connected to the intermediate portion in the arterial blood circuit for extracorporeally circulating blood of the patient during the blood purification treatment. The peristaltic pump consists of the blood pump which can cause the blood to flow in the arterial blood circuit. Therefore, it is possible to monitor a pressure which is present in the upstream side or the downstream side of the blood pump in the arterial blood circuit.

According to the invention described in the teachings herein, the blood removal state detection device can detect the blood removal state by estimating the pressure change in the liquid flow route from the distal end of the arterial blood circuit to the peristaltically-actuated tube, based on the radial displacement of the peristaltically-actuated tube which is detected by the displacement detection device when extracorporeally circulating the blood. Therefore, it is possible to monitor whether the blood removal state becomes defective and thus blood purification efficiency is degraded. Without connecting the separate device for monitoring the blood removal state to the liquid flow route, it is possible to accurately monitor the blood removal state during the blood purification treatment.

According to the invention described in the teachings herein, the blood removal state detection device has the blood removal defect ratio arithmetic device which obtains the radial displacement ratio of the peristaltically-actuated tube based on the detection value of the displacement detection device, and which obtains a blood removal defect ratio from the radial displacement ratio of the peristaltically-actuated tube by using the relationship between the pre-obtained radial displacement ratio of the peristaltically-actuated tube and the blood removal defect ratio. Therefore, it is possible to reliably understand a degree of the blood removal defect when the blood removal state is defective.

According to the invention described in the teachings herein, the actual blood flow rate arithmetic device is provided which obtains the flow rate of the blood which is actually caused to flow by the rotation of the blood pump, based on the blood removal defect ratio obtained by the blood removal defect ratio arithmetic device and the setting blood flow rate obtained by the setting rotation speed of the blood pump. Therefore, it is possible to more accurately and smoothly monitor the blood removal state.

According to the invention described in the teachings herein, is provided the informing device is provided which can provide the information under the condition that the blood removal defect ratio obtained by the blood removal defect ratio arithmetic device or the actual blood flow rate obtained by the actual blood flow rate arithmetic device is beyond the setting value which is set in advance. Therefore, it is possible to quickly notify health care workers who are present around the device of the blood removal defect, thereby enabling the health care workers to smoothly perform subsequent treatment.

According to the invention described in the teachings herein, the peristaltically-actuated tube is connected to the intermediate portion of the substitution circulation route for circulating the substitution during the blood purification treatment. The peristaltic pump consists of a substitution pump which can cause the substitution to flow in the substitution circulation route. Therefore, it is possible to monitor the pressure which is present in the upstream side or the downstream side of the substitution pump in the substitution circulation route.

According to the invention described in the teachings herein, it is possible to provide the peristaltic pump including the pressure detection device of a liquid flow route which is described in the teachings herein.

According to the invention described in the teachings herein, it is possible to provide the blood purification apparatus including the peristaltic pump described in the teachings herein.

DETAILED DESCRIPTION

Hereinafter, an embodiment of the present invention will be described in detail with reference to the drawings.

Figure 1:
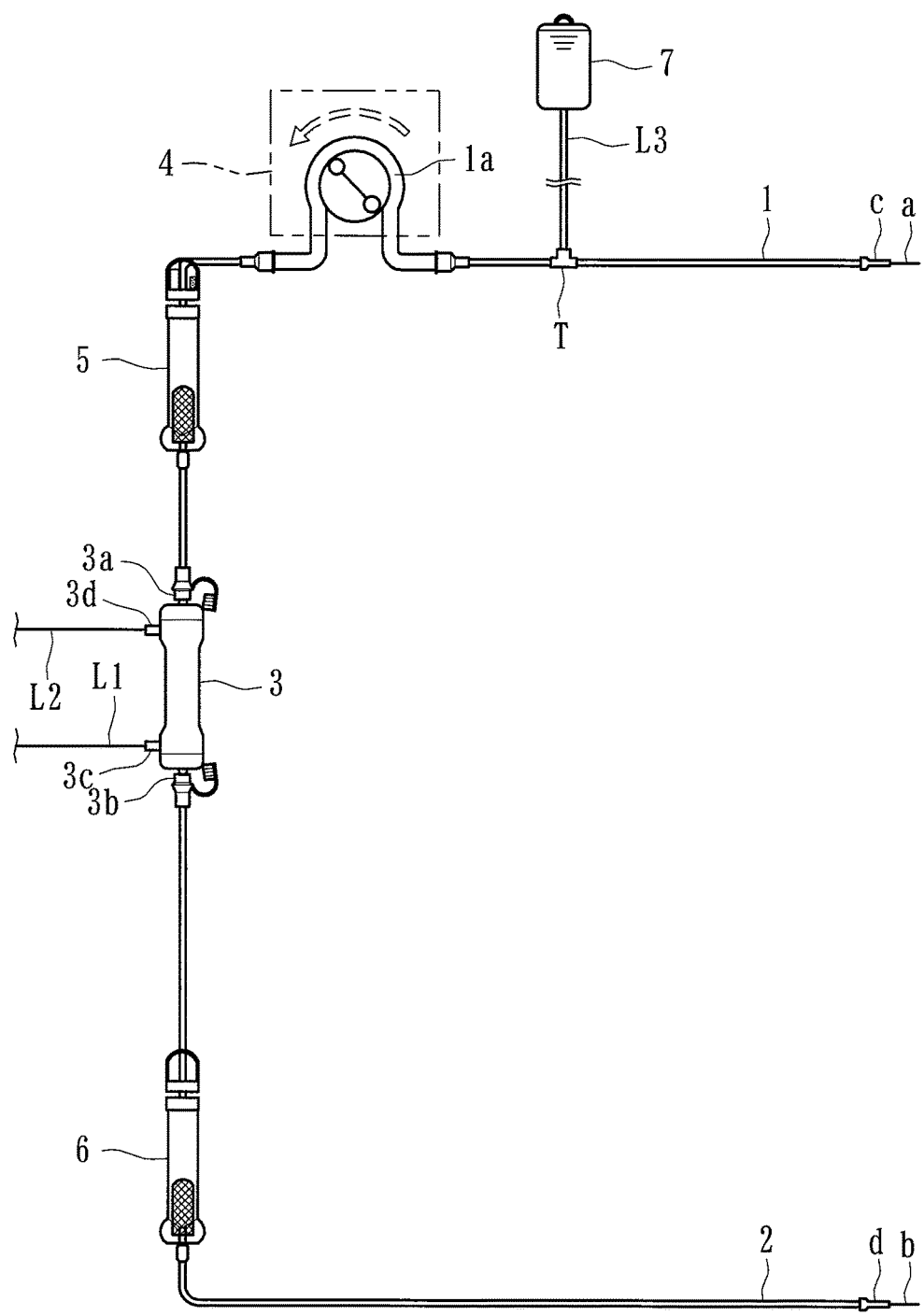
FIG. 1 is a schematic view illustrating a blood circuit which employs a pressure detection device of a liquid flow route according to a first embodiment of the present invention.

A pressure detection device according to a first embodiment detects a pressure in a blood circuit (specifically, an upstream side from a portion where a blood pump is arranged) which extracorporeally circulates blood of a patient to perform blood purification treatment (for example, hemodialysis treatment). As illustrated in FIG. 1, the blood circuit employing the pressure detection device is mainly configured to have an arterial blood circuit 1, a venous blood circuit 2 and a dialyzer 3 as a blood purifier. The arterial blood circuit 1 is equivalent to a liquid flow route, a portion of which is connected to a peristaltically-actuated tube 1a.

The arterial blood circuit 1 configures the liquid flow mute which consists of a flexible tube which can circulate a predetermined liquid. An arterial puncture needle a can be attached to a distal end of the circuit 1 via a connector c and an arterial air trap chamber 5 for removing an air bubble is connected to an intermediate portion of the circuit 1. A saline solution supplying line L3 is connected to the arterial blood circuit 1 via a T-tube T. A containing device 7 referred to as a saline bag is connected to a distal end of the saline solution supplying line L3. The saline solution supplying line L3 can be optionally opened and closed by an electromagnetic valve (not illustrated) or forceps, and is configured to be capable of supplying a saline solution inside the containing device 7 into the blood circuit.

In addition, the peristaltically-actuated tube 1a is connected to an intermediate portion (between the T-tube and the arterial air trap chamber 5) of the arterial blood circuit 1. The peristaltically-actuated tube 1a can be attached to a blood pump 4. The peristaltically-actuated tube 1a can cause an internal liquid to flow in a rotation direction of a rotor 9 by being compressed in a radial direction and peristaltically actuated in a longitudinal direction in a roller 10 (peristaltic unit) of the blood pump 4 (peristaltic pump, to be described later). The peristaltically-actuated tube 1a consists of a flexible tube which is softer and larger in diameter than other flexible tubes configuring the arterial blood circuit 1.

The venous blood circuit 2 configures a liquid flow route which consists of a flexible tube which can circulate a predetermined liquid. A venous puncture needle b can be attached to a distal end of the circuit 2 via a connector d and a venous air trap chamber 6 for removing an air bubble is connected to an intermediate portion of the circuit 2. The flexible tube configuring the venous blood circuit 2 has a material and a dimension which are substantially the same as those of the flexible tube configuring the arterial blood circuit 1. Then, the dialyzer 3 is connected to between the arterial blood circuit 1 and the venous blood circuit 2.

The dialyzer 3 is adapted so that a plurality of hollow fibers having micro holes (pores) is contained in a housing unit. The housing unit has a blood introduction port 3a, a blood discharge port 3b, a dialysate introduction port 3c and a dialysate discharge port 3d. A base end of the arterial blood circuit 1 is connected to the blood introduction port 3a and a base end of the venous blood circuit 2 is connected to the blood discharge port 3b, respectively. In addition, the dialysate introduction port 3c and the dialysate discharge port 3d are respectively connected to a dialysate introduction line L1 and a dialysate discharge line L2 which are extended from a dialysis device (not illustrated).

Then, blood of a patient which is introduced to the dialer 3 is discharged from the blood discharge port 3b through a hollow fiber membrane thereinside (blood flow route). In contrast, dialysate which is introduced from the dialysate introduction port 3c is discharged outward from the dialysate discharge port 3d through the hollow fiber membrane (dialysate flow route). In this manner, it is possible to purify the blood by transmitting waste materials of the blood passing through the blood flow route to the dialysate side, and then it is possible to return the purified blood to an internal body of the patient via the venous blood circuit 2.

Figure 2:
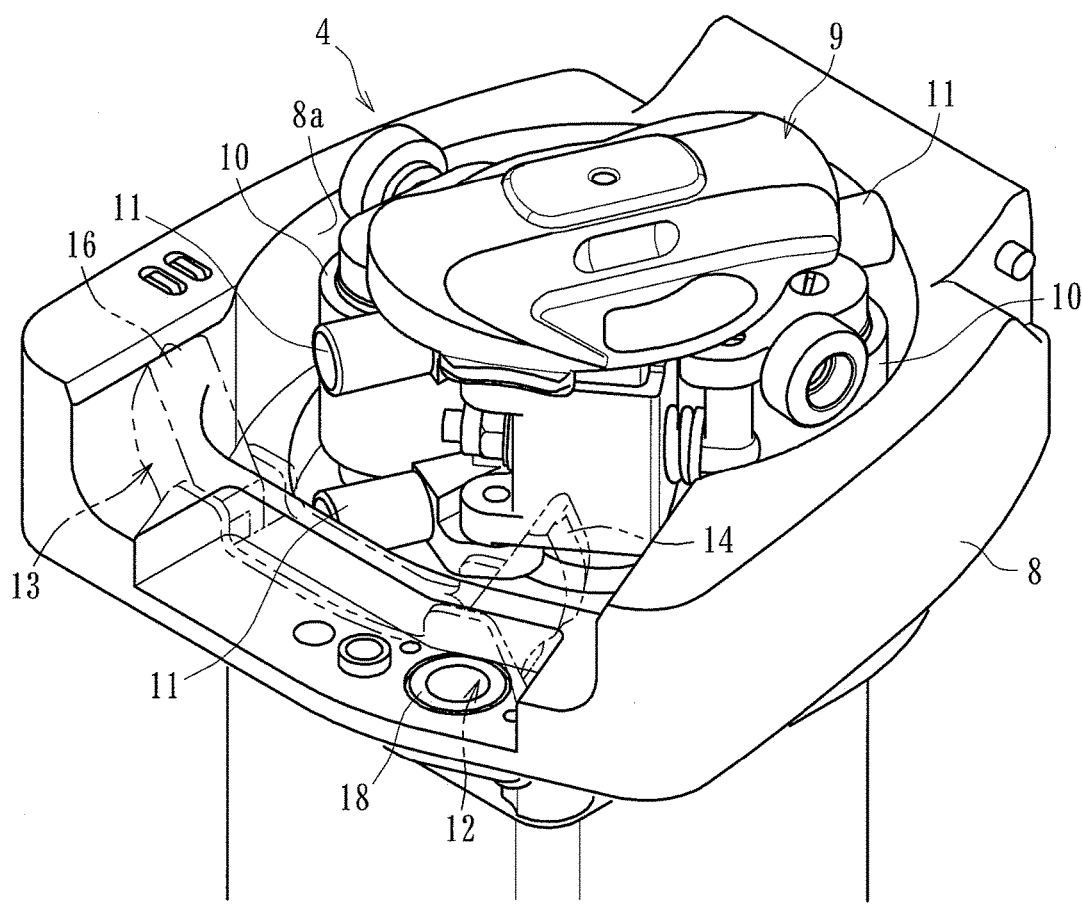
FIG. 2 is a perspective view illustrating a blood pump in which the pressure detection device is arranged.
Figure 3:
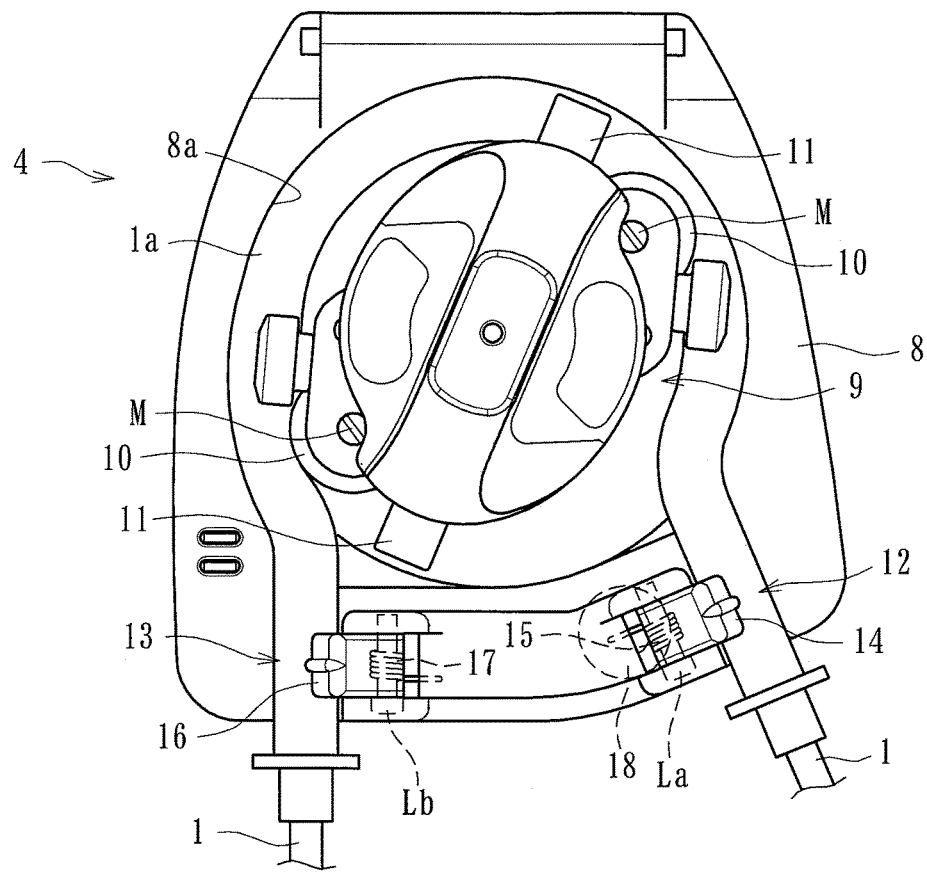
FIG. 3 is a plan view illustrating the blood pump in which the pressure detection device is arranged.
Figure 4:
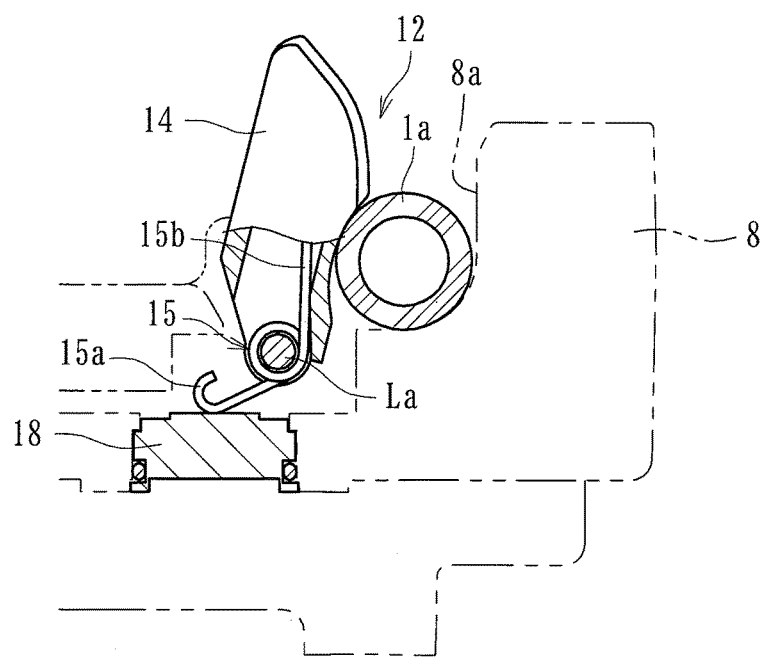
FIG. 4 is a schematic cross-sectional view illustrating the pressure detection device which is arranged in the blood pump.

Here, as illustrated in FIGS. 2 to 4, the blood pump 4 according to the present embodiment is mainly configured to include a stator 8, a rotor 9 which is rotatably driven inside the stator 8, rollers 10 (peristaltic units) formed in the rotor 9, a pair of vertically positioned guide pins 11, an upstream side gripping device 12, a downstream side gripping device 13, and a load sensor 18 as a displacement detection device. In the drawings, a cover which covers an upper portion of the stator 8 in the blood pump 4 is not illustrated.

The stator 8 has an attachment recess 8a to which the peristaltically-actuated tube 1a is attached. The stator 8 is configured to be attached along an inner peripheral wall surface having the attachment recess 8a. The rotor 9 which can be rotatably driven by a motor is arranged in a substantially center of the attachment recess 8a. A pair of rollers 10 and the guide pins 11 are arranged on a side surface of the rotor 9 (surface opposing the inner peripheral wall surface of the attachment recess 8a.

The roller 10 can be rotated about a rotation axis M formed in an outer periphery side of the rotor 9, and can cause the blood to flow inside the arterial blood circuit 1 by the peristaltically-actuated tube 1a attached to the attachment recess 8a being compressed in a radial direction and peristaltically actuated in a longitudinal direction (flowing direction of the blood) by the rotation of the rotor 9. That is, if the rotor 9 is rotatably driven by attaching the peristaltically-actuated tube is into the attachment recess 8a, the peristaltically-actuated tube 1a is compressed between the roller 10 and the inner peripheral wall surface of the attachment recess 8a, and thus can be peristaltically actuated in the rotation direction (longitudinal direction) by the rotation drive of the rotor 9. The peristaltic operation causes the blood in the arterial blood circuit 1 to flow in the rotation direction of the rotor 9, thereby enabling extracorporeal circulation of the blood inside the arterial blood circuit 1.

As illustrated in FIG. 2, the guide pins 11 consist of the pair of vertically positioned pin-shaped members which are respectively formed to protrude toward the inner peripheral wall surface of the attachment recess 8a from an upper end side and a lower end side of the rotor 9. The peristaltically-actuated tube 1a is held between the pair of vertically positioned guide pins 11. That is, when the rotor 9 is driven, the pair of vertically positioned guide pins 11 hold the peristaltically-actuated tube 1a at a normal position, and the upper side guide pin 11 holds the peristaltically-actuated tube 1a so as not to be separated upward from the attachment recess 8a.

The upstream side gripping device 12 grips the upstream side (portion to which the distal end side of the arterial blood circuit 1 is connected) of the peristaltically-actuated tube 1a attached to the attachment recess 8a of the stator 8 in the blood pump 4. As illustrated in FIGS. 2 to 4, the upstream side gripping device 12 has a gripping piece 14 which can grip the peristaltically-actuated tube 1a by pressing the peristaltically-actuated tube 1a in the radial direction, and a torsion spring 15 (biasing device) which biases the gripping piece 14 against the peristaltically-actuated tube 1a side.

As illustrated in FIG. 4, the gripping piece 14 consists of a component which can be oscillated about an oscillation axis La, is relatively strongly biased by the torsion spring 15 in a gripping direction, and can fix an upstream side portion of the peristaltically-actuated tube 1a by pressing and firmly interposing the portion therebetween. As illustrated in FIG. 4, the torsion spring 15 is attached to the oscillation axis La so as to bias the gripping piece 14, and has a fixing end 15a positioned in a fixing unit of the stator 8 (in the present embodiment, a load sensor 18 attached to the stator 8) and a pressing end 15b which presses the gripping piece 14. Instead of the torsion spring 15, other biasing devices which bias the gripping piece 14 may be used.

The downstream side gripping device 13 grips the downstream side (portion to which the base end side of the arterial blood circuit 1 is connected) of the peristaltically-actuated tube 1a attached to the attachment recess 8a of the stator 8 in the blood pump 4. The downstream side gripping device 13 has a gripping piece 16 which can grip the peristaltically-actuated tube 1a by pressing the peristaltically-actuated tube is in the radial direction, and a torsion spring 17 which biases the gripping piece 16 against the peristaltically-actuated tube 1a side.

Similar to the gripping piece 14 of the upstream side gripping device 12, the gripping piece 16 consists of a component which can be oscillated about an oscillation axis Lb, is relatively strongly biased by the torsion spring 17 in the gripping direction, and can fix a downstream side portion of the peristaltically-actuated tube 1a by pressing and firmly interposing the portion therebetween. Similar to the torsion spring 15 of the upstream side gripping device 12, the torsion spring 17 is attached to the oscillation axis Lb so as to bias the gripping piece 16, and has a fixing end positioned in the fixing unit of the stator 8 and a pressing end which presses the gripping piece 16.

The load sensor 18 as a displacement detection device can detect radial displacement of a portion gripped by the upstream side gripping device 12 in the peristaltically-actuated tube 1a. In the present embodiment, the load sensor 18 detects a load applied to the fixing end 15a side of the torsion spring 15 (biasing device), and is adapted to detect the radial displacement of the peristaltically-actuated tube 1a based on the detected load. The load sensor 18 can generate an electrical signal in response to the applied load.

That is, since the arterial puncture needle a is attached to the distal end of the arterial blood circuit 1 during the treatment, when the blood is collected from the patient to flow in the arterial blood circuit 1 (flow in an arrow direction indicating the rotation direction of the blood pump 4 in FIG. 1), a negative pressure is generated between the distal end of the arterial blood circuit 1 and the blood pump 4. If the negative pressure is generated, a liquid pressure inside the peristaltically-actuated tube 1a is decreased, and the portion gripped by the upstream side gripping device 12 in the peristaltically-actuated tube 1a is displaced (diameter is decreased) in the radial direction. Thus, the load detected by the load sensor 18 is decreased. It is possible to detect that the negative pressure is generated in the arterial blood circuit 1, by detecting the decrease in the load.

According to the above-described first embodiment, it is possible to detect the pressure of the arterial blood circuit 1 (liquid flow route) by using the load sensor 18 as the displacement detection device which detects the radial displacement of the peristaltically-actuated tube 1a. Thus, a separate device for detecting the pressure no longer needs to be connected to the arterial blood circuit 1. Therefore, it is possible to suppress the stagnation of the circulating liquid, and it is possible to reduce the manufacturing cost and the capacity (priming volume) of the arterial blood circuit 1 (blood circuit) as the liquid flow route.

In addition, the blood pump 4 includes the gripping devices (upstream side gripping device 12 and the downstream side gripping device 13) for gripping the peristaltically-actuated tube 1a attached to the blood pump 4. The load sensor 18 as the displacement detection device can detect the radial displacement of the portion gripped by the upstream side gripping device 12. Thus, the peristaltically-actuated tube 1a is attached to the blood pump 4 and is gripped by the upstream side gripping device 12 so that the peristaltically-actuated tube 1a is attached to the pressure detection device. Therefore, health care workers can reduce the burden of work.

Further, the upstream side gripping device 12 has the gripping piece 14 which can grip the peristaltically-actuated tube 1a by pressing the peristaltically-actuated tube 1a in the radial direction, and the torsion spring 15 (biasing device) which biases the gripping piece 14 against the peristaltically-actuated tube 1a. The load sensor 18 as the displacement detection device detects the load applied to the fixing end 15a side of the torsion spring 15, and detects the radial displacement of the peristaltically-actuated tube 1a based on the detected load. Therefore, the torsion spring 15 in the blood pump 4 can be provided with both of a function for generating gripping force with respect to the peristaltically-actuated tube 1a with increased force and a function for detecting the pressure of the arterial blood circuit 1.

Furthermore, the peristaltically-actuated tube 1a is connected to the intermediate portion of the arterial blood circuit 1 for extracorporeally circulating the blood of a patient during the blood purification treatment (hemodialysis treatment). The peristaltic pump which is employed consists of the blood pump 4 which can cause the blood to flow inside the arterial blood circuit 1. Therefore, it is possible to monitor the negative pressure generated in the upstream side of the blood pump 4 in the arterial blood circuit 1.

Next, a second embodiment of the present invention will be described. A pressure detection device according to the present embodiment detects a pressure in a blood circuit (specifically, an upstream side from a portion where a blood pump is arranged) for performing blood purification treatment (for example, hemodialysis treatment) by extracorporeally circulating blood of a patient. The blood circuit which is employed therein is the same as that of the above-described first embodiment. Since the blood circuit (liquid flow route and the peristaltically-actuated tube 1a) which employs the pressure detection device is the same as that illustrated in FIG. 1 of the first embodiment, description thereof will be omitted.

Figure 5:
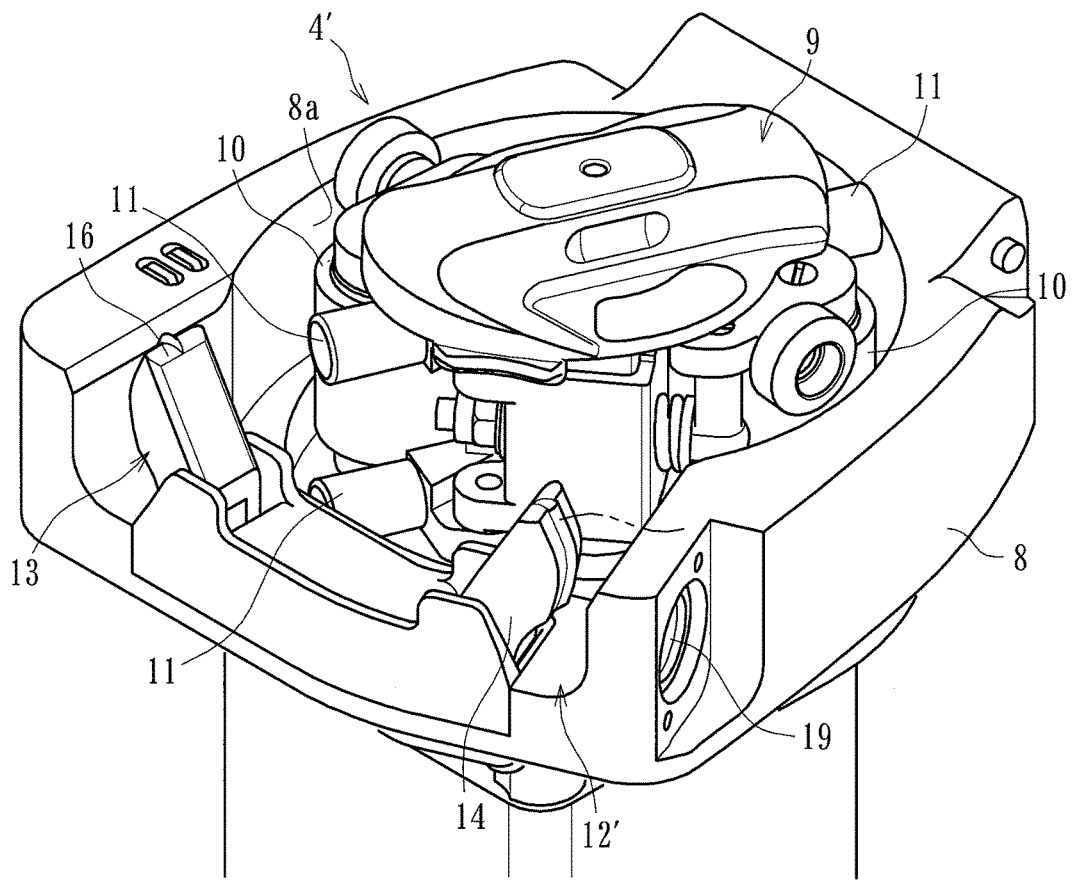
FIG. 5 is a perspective view illustrating a blood pump in which a pressure detection device of a liquid flow route according to a second embodiment of the present invention is arranged.
Figure 6:
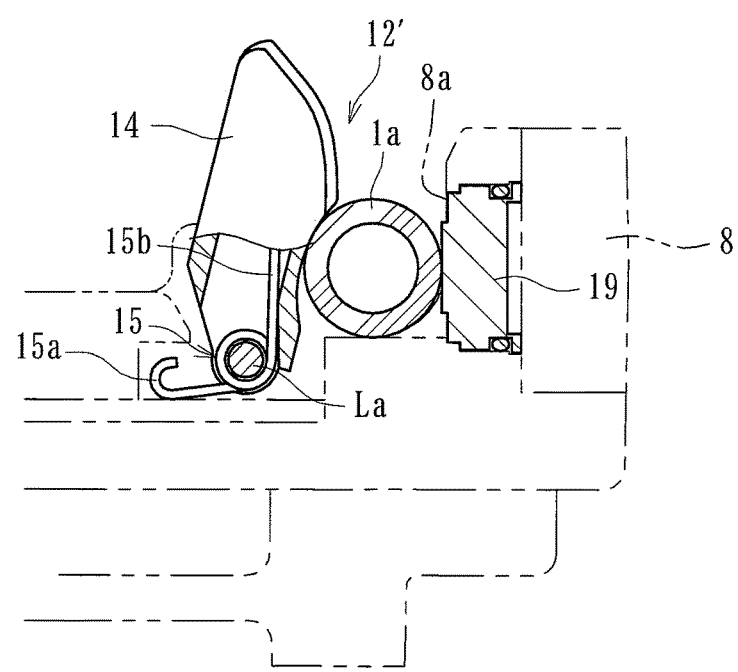
FIG. 6 is a schematic cross-sectional view illustrating the pressure detection device which is arranged in the blood pump.

As illustrated in FIGS. 5 and 6, a blood pump 4 (peristaltic pump) is mainly configured to include the stator 8, the rotor 9 which is rotatably driven inside the stator 8, the roller 10 (peristaltic unit) formed in the rotor 9, the pair of vertically positioned guide pins 11, an upstream side gripping device 12', the downstream side gripping device 13, and a pressure transducer 19 as the displacement detection device. The same reference numerals are given to the configuring components in the blood pump 4' which are the same as those in the first embodiment, and description thereof will be omitted.

The upstream side gripping device 12' is adapted to grip an upstream side (portion to which the distal end side of the arterial blood circuit 1 is connected) of the peristaltically-actuated tube 1a attached to the attachment recess 8a of the stator 8 in the blood pump 4'. As illustrated in FIG. 5, the upstream side gripping device 12' has the gripping piece 14 which can grip the peristaltically-actuated tube 1a by pressing the peristaltically-actuated tube 1a in the radial direction, and the torsion spring 15 (biasing device) which biases the gripping piece 14 against the peristaltically-actuated tube 1a.

The pressure transducer 19 as the displacement detection device can detect the radial displacement of the portion gripped by the upstream side gripping device 12' in the peristaltically-actuated tube 1a in the present embodiment, the pressure transducer 19 is arranged in a portion opposing the gripping piece 14 by interposing the peristaltically-actuated tube 1a therebetween, detects the pressure applied to the side surface of the peristaltically-actuated tube 1a pressed by the gripping piece 14, and is adapted to detect the radial displacement of the peristaltically-actuated tube 1a based on the detected pressure.

That is, when the blood is collected from the patient and is caused to flow in the arterial blood circuit 1, if the negative pressure is generated between the distal end of the arterial blood circuit 1 and the blood pump 4, the liquid pressure inside the peristaltically-actuated tube 1a is decreased, and the portion gripped by the upstream side gripping device 12' in the peristaltically-actuated tube 1a is likely to be displaced in the radial direction (diameter is likely to be decreased). Thus, an area in contact with the pressure transducer 19 is decreased and the pressure detected by the pressure transducer 19 is decreased. It is possible to detect that the negative pressure is generated in the arterial blood circuit 1, by detecting the decrease in the pressure.

According to the above-described second embodiment, the pressure transducer 19 as the displacement detection device which detects the radial displacement of the peristaltically-actuated tube 1a can detect the pressure of the arterial blood circuit 1 (liquid flow route). Thus, a separate device for detecting the pressure no longer needs to be connected to the arterial blood circuit 1. Therefore, it is possible to suppress the stagnation of the circulating liquid, and it is possible to reduce the manufacturing cost and the capacity (priming volume) of the arterial blood circuit 1 (blood circuit) as the liquid flow route.

In addition, the blood pump 4' includes the gripping devices (upstream side gripping device 12' and the downstream side gripping device 13) for gripping the peristaltically-actuated tube 1a attached to the blood pump 4'. The pressure transducer 19 as the displacement detection device can detect the radial displacement of the portion gripped by the upstream side gripping device 12'. Thus, the peristaltically-actuated tube 1a is attached to the blood pump 4' and is gripped by the upstream side gripping device 12' so that the peristaltically-actuated tube 1a is attached to the pressure detection device. Therefore, health care workers can reduce the burden of work.

Further, the upstream side gripping device 12' has the gripping piece 14 which can grip the peristaltically-actuated tube 1a by pressing the peristaltically-actuated tube 1a in the radial direction, and the torsion spring 15 (biasing device) which biases the gripping piece 14 against the peristaltically-actuated tube is side. The pressure transducer 19 as the displacement detection device is arranged in the portion opposing the gripping piece 14 by interposing the peristaltically-actuated tube is therebetween, detects the pressure applied to the side surface of the peristaltically-actuated tube is pressed by the gripping piece 14, and detects the radial displacement of the peristaltically-actuated tube is based on the detected pressure. Therefore, the displacement detection device (pressure transducer 19) in the blood pump 4' can be provided with both of a function for receiving pressing force against the peristaltically actuated tube 1a and a function for detecting the pressure of the arterial blood circuit 1.

As is apparent from the present embodiment, in the portion where the displacement detection device is positioned in the liquid flow route, the present invention is not limited to those which are actually displaced in the radial direction as in the first embodiment. The present invention includes a case where a side surface of a tube to which radially displacing force is applied is restricted and thus is not displaced, for example, such as a case where both side surfaces of a tube are restricted by and interposed between the gripping devices. That is, the present invention is advantageously applied if the radial displacement of the peristaltically-actuated tube 1a can be directly or indirectly detected. As in the present embodiment, the displacement which will be made if not restricted may be detected.

Furthermore, the peristaltically-actuated tube 1a is connected to the intermediate portion of the arterial blood circuit 1 for extracorporeally circulating the blood of the patient during the blood purification treatment (hemodialysis treatment). The peristaltic pump which is employed consists of the blood pump 4' which can cause the blood to flow inside the arterial blood circuit 1. Therefore, it is possible to monitor the negative pressure generated in the upstream side of the blood pump 4' in the arterial blood circuit 1.

According to the first embodiment and the second embodiment, it is possible to provide the peristaltic pumps (blood pumps 4 and 4') including the pressure detection device of the arterial blood circuit 1 (liquid flow route), and it is possible to provide the blood purification apparatus including the peristaltic pumps (blood pump 4 and 4'). That is, in the peristaltic pumps (blood pumps 4 and 4') according to the present invention or the blood purification apparatus including the same, it is possible to achieve advantageous effects the same as those of the first embodiment and the second embodiment. In addition, it is not necessary to provide the portion for detecting the pressure in the blood circuit side. Therefore, it is possible to use the blood circuit having no negative pressure detection unit which is referred to as a so-called pillow.

Further, the pressure is detected by detecting the displacement of the peristaltically-actuated tube 1a which is soft (that is, a nature which is rich in flexibility) and large in diameter, within the extracorporeally circulating blood circuit. Therefore, it is possible to widely set a detection range, and it is possible to further improve accuracy in detecting the pressure. In addition, it is possible to detect the displacement of the peristaltically-actuated tube 1a in a non-wetted manner (probe does not come into contact with the internally circulating liquid).

Furthermore, according to the first embodiment and the second embodiment, setting of the pressure detection device is completed by attaching the peristaltically-actuated tube to the blood pumps 4 and 4' and gripping the peristaltically-actuated tube using the gripping devices (upstream side gripping device and downstream side gripping device). Therefore, without increasing the worker's burden, it is possible to detect the pressure. That is, in the negative pressure detector (pressure detector) in the related art, it is necessary to separately mount the blood circuit or a pressure detection member on the device which detects the pressure in the blood circuit, in particular, hemodialysis facilities generally have 10 to 50 dialysis apparatuses. Therefore, if the preparing work is performed for each device, the preparing work takes time and the burden on the health care workers is increased, thereby causing mistakes in the preparing work in contrast, in the present embodiment, it is possible to reduce the burden on the worker by omitting the separate preparing work. In the present invention, without being limited to those which have the pressure detection device in the peristaltic pump as in the first embodiment and the second embodiment, a pressure detection device separate from the peristaltic pump may be used.

In addition, according to the first embodiment and the second embodiment, not only the negative, pressure but also a positive pressure can be detected. That is, it is possible to detect that the arterial blood circuit 1 (liquid flow route) has the positive pressure, by detecting the displacement which causes the diameter to be increased in addition to the displacement which causes the diameter to be decreased, out of the radial displacement of the peristaltically-actuated tube. In this manner, when the pressure detection device is applied to the blood pumps 4 and 4' as in the above-described embodiments, it is possible to detect the negative pressure of the arterial blood circuit 1 (liquid flow route between the blood pumps 4 and 4' and the arterial puncture needle a) when the blood pumps 4 and 4' are in a normal rotation. Furthermore, it is possible to detect the positive pressure of the arterial blood circuit 1 (liquid flow route between the blood pumps 4 and 4' and the arterial puncture needle a) when the blood pumps 4 and 4' are in a reverse rotation.

Next, a third embodiment of the present invention will be described. A pressure detection device according to the present embodiment is adapted to detect a blood removal state in the arterial blood circuit (specifically, a pressure of the upstream side from the portion where the blood pump is arranged) of the blood circuit for performing blood purification treatment (for example, hemodialysis treatment) by extracorporeally circulating blood of a patient. The blood circuit which employs the pressure detection device is the same as that of the first and second embodiments. Since the blood circuit which employs the pressure detection device (arterial blood circuit 1 as the liquid flow route and the peristaltically-actuated tube 1a) is the same as that illustrated in FIG. 1 of the first embodiment, and thus description thereof will be omitted.

Figure 7:
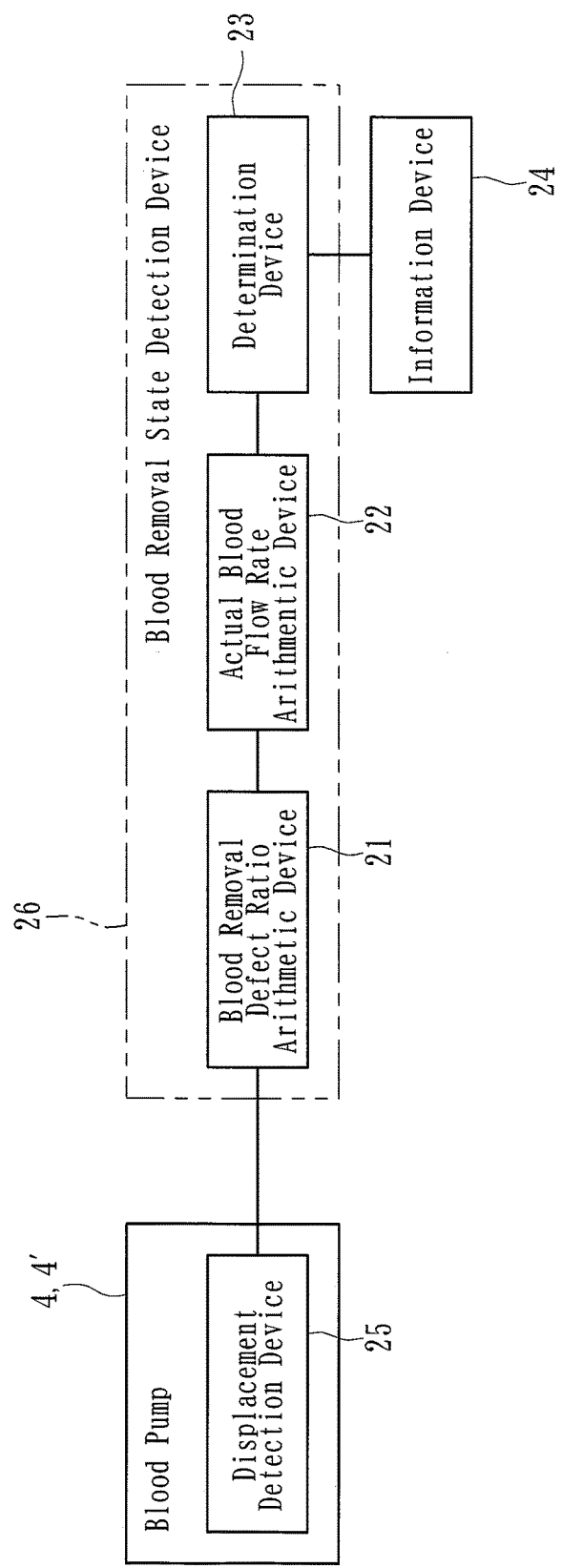
FIG. 7 is a block diagram illustrating a pressure detection device of a liquid flow route according to a third embodiment of the present invention.

More specifically, as illustrated in FIG. 7, the pressure detection device according to the present embodiment is configured to have a displacement detection device 25 arranged in the blood pumps 4 and 4 and a blood removal state detection device 26 arranged in the dialysis device, for example. Out of them, similar to the load sensor 18 (refer to FIG. 4) according to the first embodiment or the pressure transducer 19 (refer to FIG. 6) according to the second embodiment, the displacement detection device 25 is arranged in the blood pumps 4 and 4', and can detect the radial displacement of the portion gripped by the upstream side gripping devices 12 and 12' in the peristaltically-actuated tube 1a.

That is, when the blood is collected from the patient to flow in the arterial blood circuit 1 (this is referred to as "blood removal") and is extracorporeally circulated in the arterial blood circuit 1 and the venous blood circuit 2, if the negative pressure is generated between the distal end of the arterial blood circuit 1 and the blood pump 4, the liquid pressure inside the peristaltically-actuated tube 1a is decreased, and the portion gripped by the upstream side gripping devices 12 and 12 in the peristaltically-actuated tube 1a is displaced in the radial direction (diameter is decreased). Thus, the load detected by the load sensor 18 or the pressure detected by the pressure transducer 19 is decreased.

If the portion gripped by the upstream side gripping devices 12 and 12' in the peristaltically-actuated tube 1a is displaced in the radial direction, an output voltage is changed and thus it is possible to detect the radial displacement. Based on the change in the output voltage, the decrease in the load or the pressure is detected. In this manner, it is possible to detect that the negative pressure is generated between the distal end of the arterial blood circuit 1 and the peristaltically-actuated tube Is in the arterial blood circuit 1.

The displacement detection device 25 is not limited to the load sensor 18 or the pressure transducer 19 according to the first and second embodiments. If the radial displacement of the peristaltically-actuated tube Is can be directly or indirectly detected, other generic displacement detection devices may be used in addition, in the load sensor 18 or the pressure transducer 19 according to the first and second embodiments, the radial displacement of the peristaltically-actuated tube 1a is detected by detecting the radial displacement of the portion gripped by the upstream side gripping devices 12 and 12. However, the displacement of the other portions of the peristaltically-actuated tube 1a in the radial direction may be detected.

The blood removal state detection device 26 consists of a microcomputer, for example, which is electrically connected to the displacement detection device 25. Based on the radial displacement of the peristaltically-actuated tube 1a which is detected by the displacement detection device 25 during the extracorporeal circulating of the blood, the blood removal state detection device 26 can detect a blood removal state by estimating a pressure change in the liquid flow route from the distal end of the arterial blood circuit 1 to the peristaltically-actuated tube 1a. As illustrated in FIG. 7, the blood removal state detection device 26 is configured to have a blood removal defect ratio arithmetic device 21 an actual blood flow rate arithmetic device 22 and a determination device 23.

The blood removal defect ratio arithmetic device 21 obtains a radial displacement ratio of the peristaltically-actuated tube 1a based on a detection value of the displacement detection device 25, and obtains a blood removal defect ratio from the radial displacement ratio of the peristaltically-actuated tube 1a by using a relationship between the pre-obtained radial displacement ratio of the peristaltically-actuated tube 1a and the blood removal defect ratio. Here, in a state where the peristaltically-actuated tube 1a is attached to the attachment recess 8a of the blood pumps 4 and 4' and the upstream side is gripped by the upstream side gripping devices 12 and 12' (state before the blood removal), the output voltage (zero point) in the displacement detection device 25 is set to $V_0$, and in a state where the blood pumps 4 and 4' are rotated and the blood of the patient is removed (the blood of the patient is extracorporeally circulating in the blood circuit), the output voltage is set to $V_1$. In this case, the radial displacement ratio (%) of the peristaltically-actuated tube 1a is obtained by the following equation.

The radial displacement ratio (%) of the peristaltically-actuated tube 1a=$(V_1/V_0) \times 100$ (Equation 1)

Figure 8:
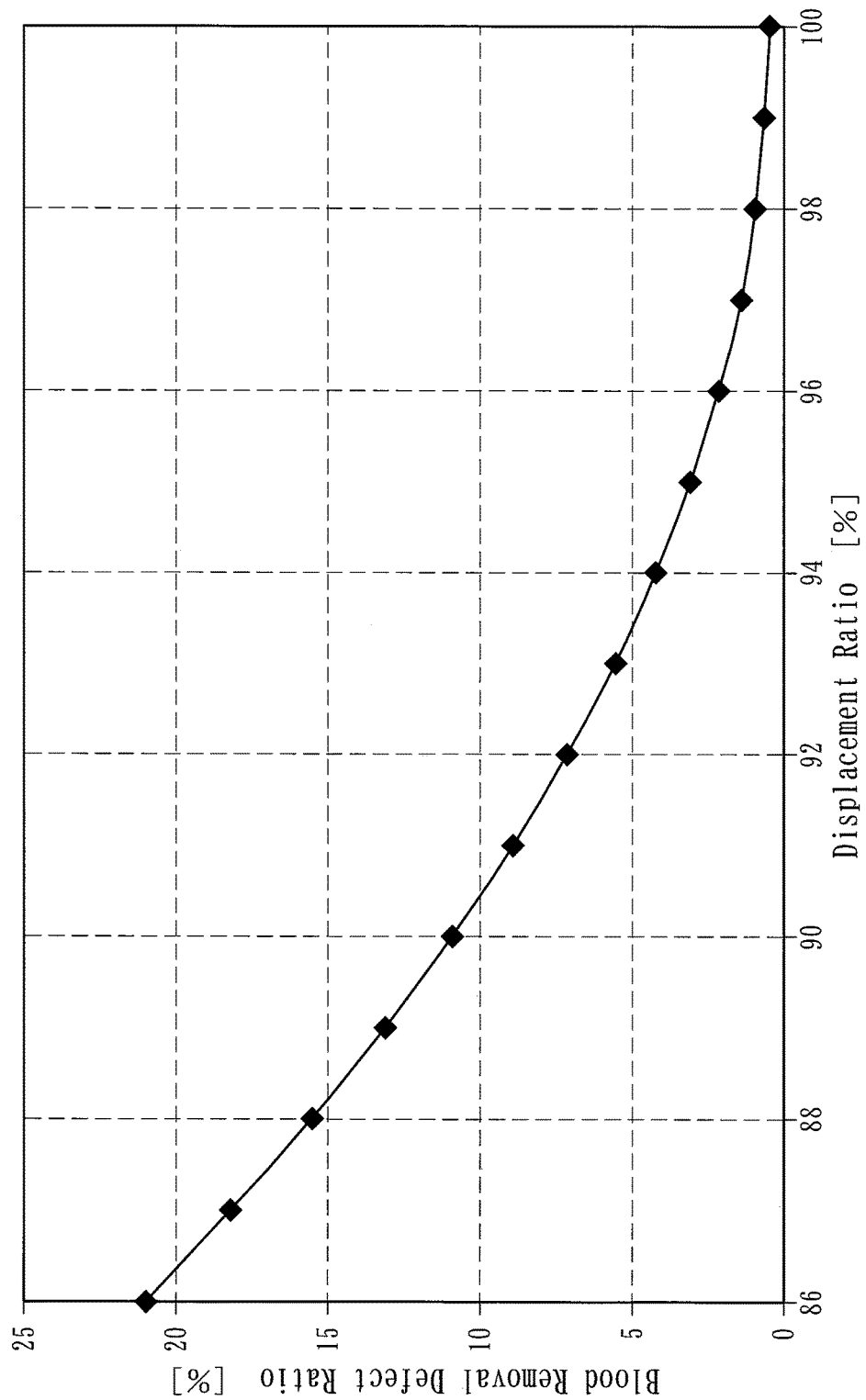
FIG. 8 is a graph illustrating a calibration curve used in the pressure detection device of the liquid flow route.

In addition, in the present embodiment, the relationship between the pre-obtained radial displacement ratio of the peristaltically-actuated tube 1a and the blood removal defect ratio is obtained from results of experiments performed in advance (experiments in which the blood removal state is arranged by actually flowing the blood in the liquid flow route equivalent to the arterial blood circuit 1 and the peristaltically-actuated tube 1a so as to obtain the relationship between the radial displacement ratio corresponding to the peristaltically-actuated tube 1a and the blood removal defect ratio). For example, as illustrated in FIG. 8, values obtained by the experiments are plotted on a graph whose horizontal axis is the radial displacement ratio (%) and vertical axis is the blood removal defect ratio (%). In this manner, in a case of the present embodiment, a calibration curve indicating the relationship between the radial displacement ratio of the peristaltically-actuated tube 1a and the blood removal defect ratio can be obtained by a quadratic curve based on the following equation 2.

The blood removal defect ratio (%)=$(10.47(X/100)^2 - 20.941(X/100)+10.47) \times 100$ ($X$ is the radial displacement ratio (%) of the peristaltically-actuated tube 1a) (Equation 2)

In the present embodiment, the relationship between the radial displacement ratio of the peristaltically-actuated tube 1a (displacement ratio (%) obtained by the equation 1) and the blood removal defect ratio (blood removal defect ratio (%) obtained by the equation 2) is obtained from the results of the experiments performed in advance. However, instead of this, the relationship may be obtained from theoretical values based on the dimension and materials of the peristaltically-actuated tube 1a and the arterial blood circuit 1 or viscosity of the blood. In addition, the relationship between the radial displacement ratio of the peristaltically-actuated tube 1a and the blood removal defect ratio is not limited to those which are illustrated by the calibration curve as in the present embodiment. For example, a map indicating the relationship between the radial displacement ratio of the peristaltically-actuated tube 1a and the blood removal defect ratio may be used.

In the blood removal defect ratio arithmetic device 21, it is possible to obtain the blood defect ratio (%) by substituting the radial displacement ratio (%) of the peristaltically-actuated tube 1a which is obtained by the equation 1 with a parameter X of the equation 2 which indicates the calibration curve, if the blood pumps 4 and 4 are rotated so that the roller 10 (peristaltic unit) peristaltically actuate the peristaltically-actuated tube 1a, the blood removal defect ratio (%) becomes zero when the negative pressure is not generated at all from the distal end of the arterial blood circuit 1 to the peristaltically-actuated tube 1s and thus only the blood having the setting flow rate is caused to flow therein. The blood removal defect ratio (%) is a value which becomes larger as the negative pressure of the portion becomes stronger (is increased) and thus the flow of the blood is below the setting flow rate.

The actual blood flow rate arithmetic device 22 obtains a flow rate of the blood (actual blood flow rate) which is actually circulated by the rotation of the blood pumps 4 and 4' based on the blood removal defect ratio (%) obtained by the blood removal defect ratio arithmetic device 21 and a setting rotation speed of the blood pumps 4 and 4' (setting rotation speed of the rotor 9). For example, after a setting blood flow rate (mL/min) is obtained based on the setting rotation speed of the blood pumps 4 and 4', it is possible to obtain an actual blood flow rate (mL/min) using the following equation.

The actual blood flow rate (mL/min)=(1-blood removal defect ratio (%)/100)×setting blood flow rate (mL/min)  (Equation 3)

The determination device 23 determines whether or not the blood removal defect ratio (%) obtained by the equation 2 using the blood removal defect ratio arithmetic device 21 or the actual blood flow rate (mL/min) obtained by the equation 3 using the actual blood flow rate arithmetic device 22 is beyond the setting value which is set in advance. When the blood removal defect ratio (%) or the actual blood flow rate (mL/min) is beyond the setting value the determination device 23 can transmit a predetermined signal to an informing device 24 so as to output an alarm or the like, The informing device 24 consists of a display device (such as an LCD) arranged in the dialysis device, a speaker or an external display lamp, for example. Under a condition that the blood removal defect ratio (%) obtained by the blood removal defect ratio arithmetic device 21 or the actual blood flow rate (mL/min) obtained by the actual blood flow rate arithmetic device 22 is beyond the setting value which is set in advance, the informing device 24 can provide information (display on the display device, output of the alarm from the speaker, lighting or blinking of the external display lamp).

For example, when the output voltage $V_0$ (zero point) of the displacement detection device 25 is 1.988 (V), the output voltage $V_1$ is 1.815 (V), the setting blood flow rate is 200 (mL/min) and a setting value for the information is 190 (mL/min), the radial displacement ratio of the peristaltically-actuated tube 1a is obtained as 91.3(%) by the equation of (1.8151/1.988)×100 (refer to the equation 1), and the blood removal defect ratio is obtained as 7.8(%) by the calibration curve (refer to the equation 2). The actual blood flow rate is obtained as 184 (mL/min) by the equation of (1−91.3/100)× 200 (refer to equation 3). Thus, the actual blood flow rate is far below the 190 (mL/min) which is the setting value for the information in this case, the informing device 24 outputs the alarm so as to provide the information to the health care workers who are present around the device.

Figure 9:
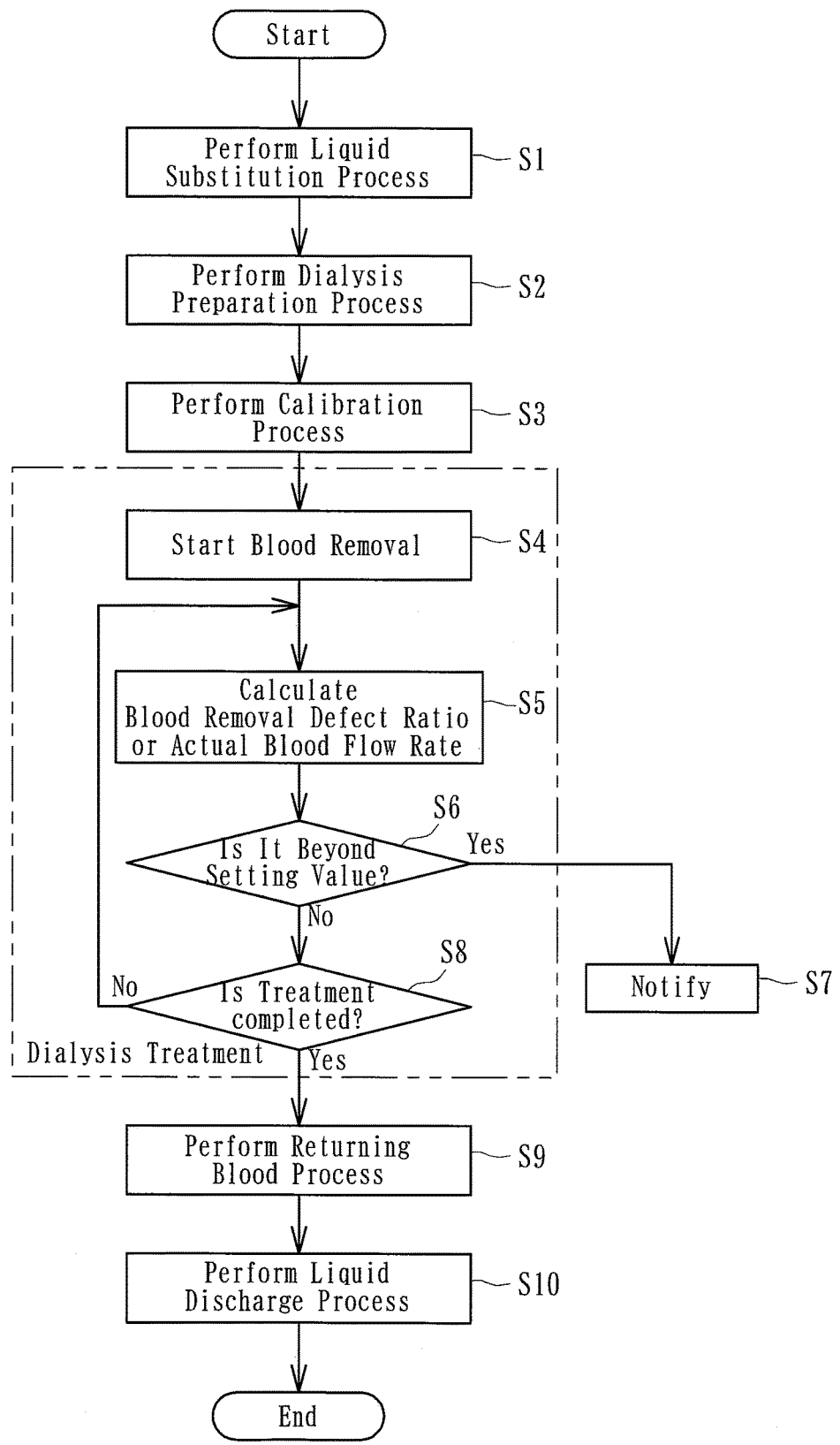
FIG. 9 is a flowchart illustrating a monitoring method using the pressure detection device of the liquid flow route.

Next, a monitoring method using the pressure detection device of the liquid flow route according to the present embodiment will be described based on a flowchart in FIG. 9.

Before starting the dialysis treatment (blood purification treatment), a liquid substitution process S1 is first performed, a tube inside the dialysis device is filled with the dialysate, and a self-diagnosis such as a tube leakage diagnosis or test is performed. Thereafter, the process proceeds to a dialysis preparation process S2 in which dialysis conditions are set, the peristaltically-actuated tube 1a is attached to the blood pump 4 in the arterial blood circuit 1 and the priming for the blood circuit or the substitution circuit (filling work of the substitution) is performed. Concurrently with the dialysis preparation process S2, the priming (gas purge) is also performed on the dialysate flow route side of the dialyzer 3.

If the dialysis preparation process S2 is completed, the process proceeds to a calibration process S3 and obtains the output voltage (zero point) $V_0$ from the displacement detection device 25. Thereafter, the arterial puncture needle a and the venous puncture needle b puncture the patient, the blood pump 4 is rotated and the rotor 9 is rotatably driven to start the blood removal (to start the blood removal 54). The blood of the patient is extracorporeally circulated via the arterial blood circuit 1 and the venous blood circuit 2. In this manner, the blood during the extracorporeal circulating is purified by the dialyzer 3 to perform the dialysis treatment (blood purification treatment).

Then, after starting the blood removal, the blood removal state detection device 26 obtains the blood removal defect ratio (%) or the actual blood flow rate (mL/min) (S5). That is, in S5, the output voltage $V_1$ is detected in the displacement detection device 25 after starting the blood removal, and based on the output voltage $V_1$ and the output voltage $V_0$ obtained in the calibration process S3, the radial displacement ratio of the peristaltically-actuated tube 1a is obtained. Thereafter, it is possible to calculate the blood removal defect ratio (%) in the blood removal defect ratio arithmetic device 21 by using the calibration curve (refer to FIG. 8) which is obtained in advance. Based on the blood removal defect ratio (%) and the setting blood flow rate obtained from the setting rotation speed of the blood pumps 4 and 4, it is possible to calculate the actual blood flow rate (mL/min) by using the actual blood flow rate arithmetic device 22.

Thereafter, the determination device 23 determines whether or not the blood removal defect ratio (%) or the actual blood flow rate (mL/min) which is calculated in S5 is beyond the setting value which is set in advance (S6). When it is beyond the setting value, the process proceeds to S7 so that the informing device 24 performs the predetermined information. When it is not beyond the setting value, the process proceeds to S8 so as to determine whether or not the dialysis treatment is completed. In S8, if it is determined that the dialysis treatment is not completed, the process returns to S5 so that the calculation and the determination are performed again in S5 and S6.

In contrast, in S8, if it is determined that the dialysis treatment is completed, the process proceeds to S9. Then, after passing through a returning blood process S9 (process for returning the blood inside the blood circuit to the internal body of the patient), a liquid discharge process 310 for discharging the liquid of the dialyzer 3 is performed and a series of controls are completed. When passing through a series of processes, in the dialysis treatment (blood purification treatment), it is possible to monitor the blood removal state based on the blood removal defect ratio or the actual blood flow rate. In addition, the calibration is performed in the calibration process 33 for each dialysis treatment (blood purification treatment). Therefore, it is possible to suppress an error due to individual differences between the peristaltically-actuated tube 1a and the displacement detection device 25 (for example, the load sensor 18 according to the first embodiment or the pressure transducer 19 according to the second embodiment) or an attachment error occurring when the peristaltically-actuated tube 1a is attached to the blood pump 4.

According to the third embodiment, based on the radial displacement of the peristaltically-actuated tube 1a which is detected by the displacement detection device 25 during the extracorporeal circulating of the blood, the blood removal state detection device 26 can detect the blood removal state by estimating the pressure change in the liquid flow route between the distal end of the arterial blood circuit 1 and the peristaltically-actuated tube 1a. Therefore, it is possible to monitor whether the blood removal state is defective and the blood purification efficiency is degraded. Without connecting a separate device for monitoring the blood removal state to the liquid flow route, it is possible to accurately monitor the blood removal state during the blood purification treatment.

In addition, the blood removal state detection device 26 according to the present embodiment has the blood removal defect ratio arithmetic device 21 which obtains the radial displacement ratio of the peristaltically-actuated tube 1a based on the detection value of the displacement detection device 25, and which obtains the blood removal defect ratio from the radial displacement ratio of the peristaltically-actuated tube 1a by using the relationship between the pre-obtained radial displacement ratio of the peristaltically-actuated tube 1a and the blood removal defect ratio. Therefore, it is possible to reliably understand a degree of the blood removal defect when the blood removal state is defective.

Further, according to the present embodiment, based on the blood removal defect ratio obtained by the blood removal defect ratio arithmetic device 21 and the setting blood flow rate obtained from the setting rotation speed of the blood pump 4 and 4', the actual blood flow rate arithmetic device 22 obtains the flow rate of the blood which is actually circulated by the rotation of the blood pumps 4 and 4' (that is, an peristaltic actuation accompanied by the rotation drive of the rotor 9). Therefore, it is possible to more accurately and smoothly monitor the blood removal state.

Furthermore, according to the present embodiment, there is provided the informing device 24 that can provide the information under the condition that the blood removal defect ratio obtained by the blood removal defect ratio arithmetic device 21 or the actual blood flow rate obtained by the actual blood flow rate arithmetic device 22 is beyond the setting value which is set in advance. Therefore, it is possible to quickly notify health care workers around the device of the blood removal defect, thereby enabling the health care workers to smoothly perform subsequent treatment.

Figure 10:
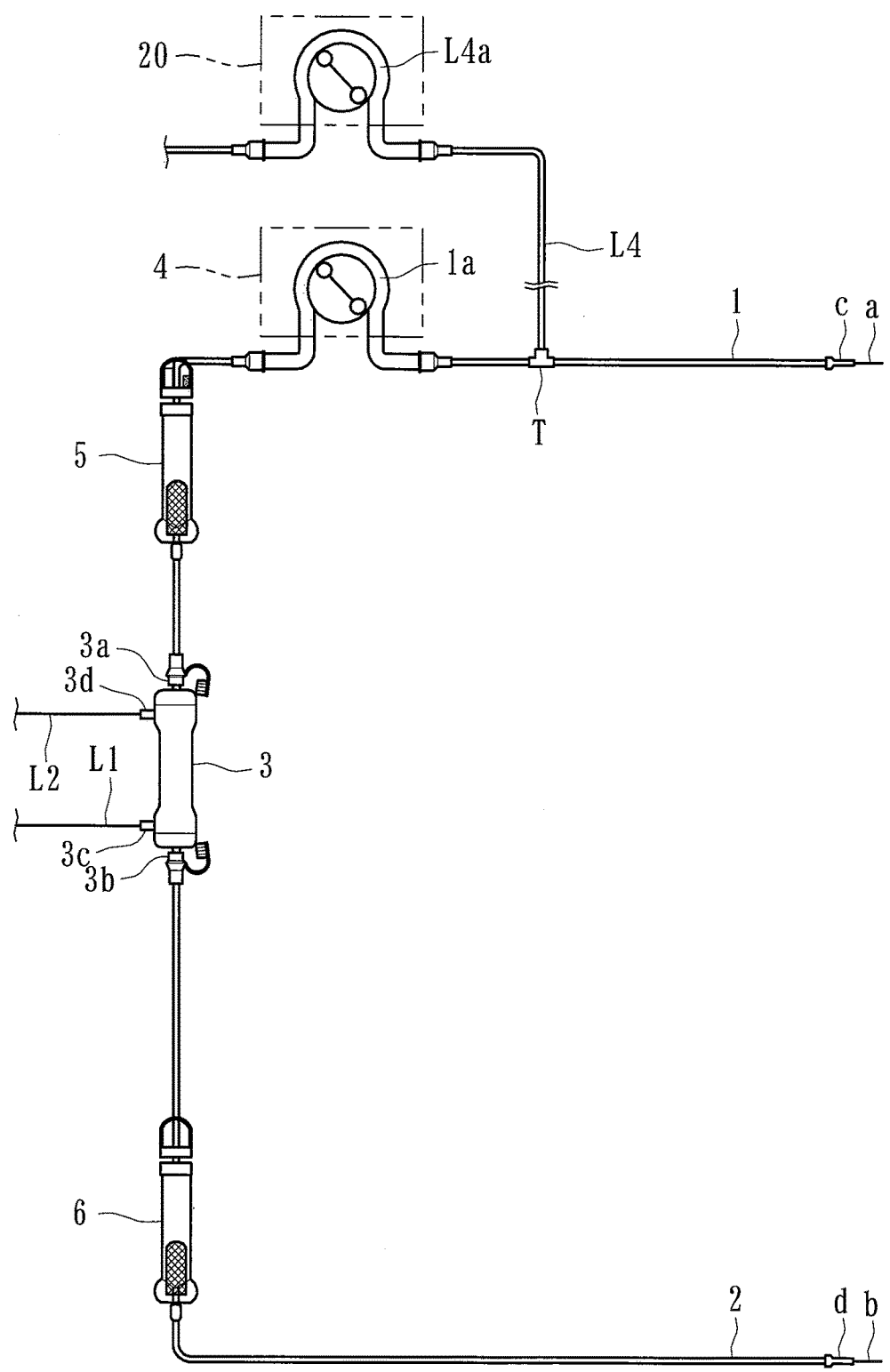
FIG. 10 is a schematic view illustrating a blood circuit which employs a pressure detection device of a flow route according to another embodiment of the present invention.

Hitherto, the present embodiments have been described, but the present invention is not limited thereto. For example, instead of the blood pumps according to the first and second embodiments, the present invention can be applied to other peristaltic pumps (however, in the third embodiment, the blood pump is limited thereto). For example, as illustrated in FIG. 10, a peristaltically-actuated tube L4a may be connected to an intermediate portion of a substitution circulation route L4 for circulating the substitution during the blood purification treatment (for example, the hemodialysis treatment), and a peristaltic pump may consist of a substitution pump 20 which can cause the substitution to flow inside the substitution circulation route L4. It is possible to supply the substitution (physiological saline solution or dialysate) to the arterial blood circuit 1 via the substitution circulation route L4 by using the rotation of the substitution pump 20. It is possible to monitor the negative pressure generated in the upstream side of the substitution pump 20 in the substitution circulation route L4a.

In addition, in the above-described embodiments, the displacement detection device consists of the load sensor 18 or the pressure transducer 19, to detect the load or the pressure, and to detect the radial displacement of the peristaltically-actuated tube 1a based on the detected load or the detected pressure, but the present invention is not limited thereto. For example, the configuration may be made such that the displacement (dimension change) of the peristaltically-actuated tube 1a can be directly detected. Further, in the above-described embodiments, the liquid flow route which is employed is adapted to be the arterial blood circuit 1. However, if the peristaltically-actuated tube 1a is connected to a portion of the liquid flow route, any type of liquid flow route may be employed.

Furthermore, in the above-described embodiments, any pressure detection device can detect the negative pressure of the upstream side in the peristaltic pump (blood pumps 4 and 4 or substitution pump 20). However, any desired negative pressure of the upstream side and the downstream side in the peristaltic pump may be detected. For example, the gripping device in the peristaltic pump may include the upstream side gripping device which grips the upstream side of the peristaltically-actuated tube and the downstream side gripping device which grips the downstream side of the peristaltically-actuated tube. The displacement detection device (other devices which can detect the displacement of the pressure transducer or the peristaltically-actuated tube) may be arranged in any one of the upstream side gripping device and the downstream side gripping device according to the portion where the pressure is detected in the liquid flow route (arterial blood circuit 1 or other liquid flow routes to which the peristaltically-actuated tube is connected). In this case, it is possible to more accurately detect the pressure of a desired portion in the liquid flow route.

If a pressure detection device of a liquid flow route includes a displacement detection device which detects radial displacement of a peristaltically-actuated tube, the pressure detection device can also be applied to those which have different outer shapes or other additional functions.

REFERENCE SIGN LIST 1. arterial blood circuit (liquid flow route)
1a peristaltically-actuated tube
2 venous blood circuit
3 dialyzer (blood purifier)
4, 4' blood pump (peristaltic pump)
5 arterial air trap chamber
6 venous air trap chamber
7 containing device
8 stator
9 rotor
10 roller (peristaltic unit)
11 guide pin
12, 12' upstream side gripping device
13 downstream side gripping device
14 gripping piece
15 torsion spring (biasing device)
16 gripping piece
17 torsion spring
18 load sensor (displacement detection device)
19 pressure transducer (displacement detection device)
20 substitution pump (peristaltic pump)
21 blood removal defect ratio arithmetic device
22 actual blood flow rate arithmetic device
23 determination device
24 informing device L4 substitution circulation route
L4a peristaltically-actuated tube

The invention claimed is:

1. A pressure detection comprising:
a displacement detection device that detects radial displacement of a peristaltically-actuated tube;
wherein the pressure detection device is in communication with a liquid flow route that comprises:
a peristaltically-actuated tube, and
a flexible tube with a portion that is connected to the peristaltically actuated tube so that the displacement detection device detects a pressure of the liquid flow route;
wherein the peristaltically-actuated tube is compressed in a radial direction so that an internal liquid flows in a longitudinal direction by a peristaltic unit of a peristaltic pump and circulates a liquid;
wherein the peristaltic pump includes a gripping device which grips the peristaltically-actuated tube attached to the peristaltic pump,
wherein the gripping device includes an oscillation axis and a gripping piece which is oscillatable around the oscillation axis; and
wherein the displacement detection device detects radial displacement of a portion of the peristaltically-actuated tube gripped by the gripping device.

2. The pressure detection device according to claim 1,
wherein the gripping device has a gripping piece which grips the peristaltically-actuated tube by radially pressing the peristaltically-actuated tube and a biasing device which biases the gripping piece against the peristaltically-actuated tube side, and
wherein the displacement detection device detects a load applied to a fixing end side of the biasing device and detects the radial displacement of the peristaltically-actuated tube based on the detected load.

3. The pressure detection device according to claim 1,
wherein the gripping device has a gripping piece which grips the peristaltically-actuated tube by radially pressing the peristaltically-actuated tube and a biasing device which biases the gripping piece against the peristaltically-actuated tube side, and
wherein the displacement detection device is arranged in a portion opposing the gripping piece by interposing the peristaltically-actuated tube therebetween, detects a pressure applied to a side surface of the peristaltically-actuated tube pressed by the gripping piece, and detects the radial displacement of the peristaltically-actuated tube based on the detected pressure.

4. The pressure detection device according to claim 1,
wherein the peristaltically-actuated tube includes an upstream side from the peristaltic pump and a downstream side from the peristaltic pump;
wherein the gripping device has an upstream side gripping device which grips an upstream side of the peristaltically-actuated tube and a downstream side gripping device which grips a downstream side of the peristaltically-actuated tube, and
wherein the displacement detection device is arranged in either the upstream side gripping device or the downstream side gripping device according to a portion for detecting a pressure of the liquid flow route.

5. The pressure detection device according to claim 1,
wherein the peristaltically-actuated tube is connected to an intermediate portion in an arterial blood circuit for extracorporeally circulating blood of a patient during blood purification treatment; and
wherein the intermediate portion is between a T-tube and an arterial air trap chamber of the arterial blood circuit; and
wherein the peristaltic pump consists of a blood pump which causes the blood to flow in the arterial blood circuit.

6. The pressure detection device according to claim 1,
wherein the peristaltically-actuated tube is connected to an intermediate portion of a substitution circulation route for circulating a substitution during blood purification treatment, and
wherein the substitution circulation route is connected to an arterial blood circuit; and
wherein the peristaltic pump consists of a substitution pump which causes the substitution to flow in the substitution circulation route.

7. A peristaltic pump comprising: the pressure detection device according to claim 1.

8. A blood purification apparatus comprising: the peristaltic pump according to claim 7.

9. The pressure detection device according to claim 2,
wherein the peristaltically-actuated tube includes an upstream side from the peristaltic pump and a downstream side from the peristaltic pump;
wherein the gripping device has an upstream side gripping device which grips an upstream side of the peristaltically-actuated tube and a downstream side gripping device which grips a downstream side of the peristaltically-actuated tube, and
wherein the displacement detection device is arranged in either the upstream side gripping device or the downstream side gripping device according to a portion for detecting a pressure of the liquid flow route.

10. The pressure detection device according to claim 3,
wherein the peristaltically-actuated tube includes an upstream side from the peristaltic pump and a downstream side from the peristaltic pump;
wherein the gripping device has an upstream side gripping device which grips an upstream side of the peristaltically-actuated tube and a downstream side gripping device which grips a downstream side of the peristaltically-actuated tube, and
wherein the displacement detection device is arranged in either the upstream side gripping device or the downstream side gripping device according to a portion for detecting a pressure of the liquid flow route.

11. The pressure detection device according to claim 2,
wherein the peristaltically-actuated tube is connected to an intermediate portion of a substitution circulation route for circulating a substitution during blood purification treatment, and
wherein the substitution circulation route is connected to an arterial blood circuit; and
wherein the peristaltic pump consists of a substitution pump which causes the substitution to flow in the substitution circulation route.

12. A peristaltic pump comprising: the pressure detection device according to claim 11.

13. A blood purification apparatus comprising: the peristaltic pump according to claim 12.

14. The pressure detection device according to claim 2,
wherein the gripping piece is substantially perpendicular to the displacement detection device.

15. A pressure detection comprising:
a displacement detection device that detects radial displacement of a peristaltically-actuated tube;

wherein the pressure detection device is in communication with a liquid flow route that comprises:
a peristaltically-actuated tube, and
a flexible tube with a portion that is connected to the peristaltically-actuated tube so that the displacement detection device detects a pressure of the liquid flow route;
wherein the peristaltically-actuated tube is compressed in a radial direction so that an internal liquid flows in a longitudinal direction by a peristaltic unit of a peristaltic pump and circulates a liquid;
wherein the peristaltic pump includes a gripping device which grips the peristaltically-actuated tube attached to the peristaltic pump and wherein a portion of peristaltically-actuated tube gripped by the gripping device is free of contact by both the gripping device and peristaltic pump, and
wherein the gripping device includes an oscillation axis and a gripping piece which is oscillatable around the oscillation axis; and
wherein the displacement detection device detects radial displacement of a portion of the peristaltically-actuated tube gripped by the gripping device.

\* \* \* \* \*